(12) United States Patent
Hovinen et al.

(10) Patent No.: US 7,381,420 B2
(45) Date of Patent: Jun. 3, 2008

(54) LABELING REACTANT

(75) Inventors: Jari Hovinen, Raisio (FI); Jari Peuralahti, Turku (FI); Veli-Matti Mukkala, Kaarina (FI)

(73) Assignee: Wallac Oy, Turku (FI)

( * ) Notice: Subject to any disclaimer, the term of this patent is extended or adjusted under 35 U.S.C. 154(b) by 0 days.

(21) Appl. No.: 11/607,045

(22) Filed: Dec. 1, 2006

(65) Prior Publication Data

US 2007/0134162 A1    Jun. 14, 2007

Related U.S. Application Data

(60) Provisional application No. 60/748,195, filed on Dec. 8, 2005.

(30) Foreign Application Priority Data

Dec. 8, 2005   (FI) .............................. 20055653

(51) Int. Cl.
| | |
|---|---|
| A61K 47/00 | (2006.01) |
| C07C 69/74 | (2006.01) |
| C07C 61/00 | (2006.01) |
| C07C 61/08 | (2006.01) |
| C07C 51/58 | (2006.01) |
| C07C 53/38 | (2006.01) |
| C07C 55/36 | (2006.01) |
| C07C 57/64 | (2006.01) |
| C07C 59/00 | (2006.01) |
| C07C 62/00 | (2006.01) |
| C07C 63/00 | (2006.01) |
| C07C 65/00 | (2006.01) |

(52) U.S. Cl. .......................... 424/439; 560/1; 562/400; 562/840; 562/849

(58) Field of Classification Search .................... 560/1; 562/400, 840, 849
See application file for complete search history.

(56) References Cited

U.S. PATENT DOCUMENTS

| | | | |
|---|---|---|---|
| 4,831,175 A | 5/1989 | Gansow et al. | |
| 5,637,759 A * | 6/1997 | Hearst et al. | ............... 560/159 |
| 5,650,134 A | 7/1997 | Albert et al. | |
| 5,693,309 A | 12/1997 | Deutsch et al. | |
| 6,306,993 B1 * | 10/2001 | Rothbard et al. | ........... 526/304 |
| 6,512,092 B2 * | 1/2003 | Falb et al. | .................. 530/333 |
| 2004/0057903 A1 | 3/2004 | Hancu et al. | |

FOREIGN PATENT DOCUMENTS

| | | |
|---|---|---|
| AU | 10675/95 | 6/1995 |
| DE | 43 41 724 A1 | 6/1995 |
| WO | 03/011115 A2 | 2/2003 |

OTHER PUBLICATIONS

Wen et al. (Bioconjugate Chem 2004, 15, 1408-1415).*
John S. Davies, et al., "Synthesis of $N^\alpha$-BOC-$N^\epsilon$-Tetrabenzyl-DTPA- L -Lysine and $N^\alpha$-FMOC- $N^\epsilon$-Tetra-t-Butyl-DTPA-L-Lysine, Building Blocks for Solid Phase Synthesis of DTPA-Containing Peptides", Journal of Peptide Science, 2002, vol. 8, pp. 663-670 (cited in Finnish Office Action).
Donald T. Corson et al., "Efficient Multigram Synthesis of the Bifunctional Chelating Agent (S)-1-p-Isothiocyanatobenzyl-Diethylenetetraminepentaacetic Acid", Bioconjugate Chem., 2000, vol. 11, pp. 292-299.
Lassi Jaakkola et al., "Labeling of Proteins and Oligopeptides With Luminescent Lanthanide(III) Chelates", Journal of Peptide Science, 2006, vol. 12, pp. 199-205.
Anil Kumar Mishra et al., Convenient Route for Synthesis of Bifuncitonal Chelating Agent: 1-(p-Aminobenzyl)Ethylenediaminetetramethylphosphonic Acid-Folate Conjugate (Am-Bz-EDTMP-Folate), Chemistry Letter, 2005, vol. 34, No. 8, pp. 1098-1099.
Jari Peuralahti et al., "Synthesis of Building Blocks for Solid-Phase Introduction of Diethylenetriaminepentaacetic Acid (DPTA) to Oligonucleotides and Oligopeptides", Bioconjugate Chem., 2006, pp. 855-859.
Jari Peurralahti et al., "Introduction of Lanthanide(III) Chelates to Oligopeptides on Solid Phase", Bioconjugate Chem., 2002, vol. 13, pp. 870-875.
Finnish Office Action dated Aug. 31, 2006.

* cited by examiner

*Primary Examiner*—Michael G. Hartley
*Assistant Examiner*—Melissa Perreira
(74) *Attorney, Agent, or Firm*—Buchanan Ingersoll & Rooney PC

(57) ABSTRACT

This invention concerns novel labeling reactants suitable for labeling of a biospecific binding reactant using solid-phase synthesis. The novel reactants are derivatives of diethylenetriaminepentaacetic acid (DTPA), wherein a suitable group is linked to the DTPA molecule, thus allowing site specific introduction of the ligand of the derivatives to bioactive molecules on solid phase in an oligopeptide synthesizer.

1 Claim, No Drawings

LABELING REACTANT

FIELD OF THE INVENTION

This invention relates to novel derivatives of diethylenetriaminepentaacetic acid which allow site specific introduction of the ligand of said derivatives to bioactive molecules on solid phase.

BACKGROUND OF THE INVENTION

The publications and other materials used herein to illuminate the background of the invention, and in particular, cases to provide additional details respecting the practice, are incorporated by reference.

Because of its excellent metal chelating properties diethylenetriaminepentaacetic acid (DTPA) is one of the most widely used organic ligands in magnetic resonance imaging (MRI) and positron emission tomography (PET) [Aime, S., Botta, M., Fasano, M. and Terrano, E. 1998, Chem. Soc. Rev., 27, 19, Caravan, P., Ellison, J. J., McMurry, T. J. and Lauffer, R. B., 1999, Chem. Rev., 99, 2293, Woods, M., Kovacs, Z. and Sherry, A. D., 2002, J. Supramol. Chem., 2, 1]. Indeed, the first FDA approved contrast agent in clinical use is the $Gd^{3+}$ DTPA chelate [Runge, V. M., 2000, J. Magn. Res. Imaging, 12, 205.]. The corresponding $^{111}$In and $^{68}$Ga chelates, in turn, are suitable for PET applications [Anderson, C. J. and Welch, M. J., 1999, Chem. Rev. 99, 2219], while $Eu^{3+}$, $Tb^{3+}$, $Sm^{3+}$ and $Dy^{3+}$ chelates can be used in applications based on dissosiation enhanced lanthanide fluorescence immunoassay (DELFIA) [PCT WO 03/076939A1]. $^{99m}$Tc DTPA in turn, is suitable for single positron emission computed tomography (SPECT) [Lorberboym, M., Lampl, Y. and Sadeh, M., 2003, J. Nucl. Med. 44, 1898, Galuska, L., Leovey, A., Szucs-Farkas, Z., Garai, I., Szabo, J., Varga, J. and Nagy, E. V., 2002, Nucl. Med. Commun. 23, 1211]. Bioactive molecules labeled with $^{111}$In or $^{117m}$Sn DTPA may find applications as target-specific radiopharmaceuticals [Volkert, W. A. and Hoffman, T. J., 1999, Chem. Rev. 99, 2269].

In several applications, covalent conjugation of DTPA to bioactive molecules is required. Often, isothiocyanato, N-hydroxysuccinimide or maleimide derivatives of the chelate are used in the labeling the target molecules such as oligonucleotides and oligopeptides. Several bifunctional DTPA derivatives are currently commercially available. Because in all of these cases the labeling reaction is performed in the presence of an excess of an activated label, laborious purification procedures cannot be prevented. Especially, when attachment of several label molecules is needed, purification and characterization of the desired biomolecule conjugate may be extremely difficult.

The purification problems can be avoided by performing the labeling reaction on solid phase. Hence, most of the impurities can be removed by washings when the biomolecule conjugate is still anchored to the solid support, and after release to the solution, only one chromatographic purification is needed. Several such blocks have been published. They include organic dyes [Loshe, J., Nielsen, P. E., Harrit, N. and Dahl, O., 1997, Bioconjugate Chem. 8, 503, McCafferty, D. G., Bishop, B. M., Wall, C. G., Hughes, S. G., Mecklenberg, S. L., Meyer, T. J., and Erickson, D. W., 1995, Tetrahedron, 51, 1093, WO 96/03409, Cuppoletti, A., Cho, Y., Park, J.-C., Strässler, G. and Kool, E. T. 2005, Bioconjugate Chem. 16, 528, Bethelot, T., Lain, G., Latxague, L. and Deleris, G., 2004, J. Fluorescence, 14, 671], derivatives of EDTA [Sluka, J. P., Griffin, J. H., Mack, D. P. and Dervan, P. B. 1990, J. Am. Chem. Soc, 112, 6369, Arya, R. and Gariepy, J. 1991, Bioconjugate Chem., 2, 323, Cuenoud, B. and Schepartz, A. 1991, Tetrahedron, 47, 2535, Rana, T. M., Ban, M. and Hearst, J. E., 1992, Tetrahedron Lett, 33, 4521, Song, A. I. and Rana, T. A., 1997, Bioconjugate Chem., 8, 249, Davies, J. C., Al-Jamri, L., 2002, J. peptide Sci., 8, 663, U.S. Pat. No. 5,637,759], DOTA [Bhorade, R., Weissleder, R., Nakakoshi, T., Moore, A. and Tung, C.-H., 2000, Bioconjugate Chem., 11, 301., Gallazzi, F., Wang, Y., Jia, F., Shenoy, N., Landon, L. A., Hannink, M., Lever, S. Z. and Lewis, M. R. 2003, Bioconjugate Chem., 14, 1083.] and luminescent and non-luminescent lanthanide chelates (U.S. Pat. No. 6,080,839; U.S. Pat. No. 6,949,696; Peuralahti, J., Hakala, H., Mukkala, V.-M., Hurskainen, P., Mulari, O. and Hovinen, J. 2002 Bioconjugate Chem. 13, 876.].

Although DTPA molecule is known for decades, and although reagents for solid phase oligonucleotide derivatization with DTPA has been demonstrated [U.S. Pat. No. 6,949,639], no reactants which allow its direct solid phase conjugation to oligopeptides have been synthesized. The solid phase methods published involve synthesis of oligopeptides, where one ε-amino group of lysine is selectively deprotected while the oligomer is still anchored to the resin [Handl, H. L., Vagner, J., Yamamura, H. I., Hruby, V. J. and Gilles, R. J. 2005, Anal. Biochem. 343, 299, Nagy, I. B., Vagra, I. and Hudecz, F, 2000, Anal. Biochem., 287, 17] Then, an activated DTPA molecule (as an anhydride or an HOBt ester) is coupled to the primary amino function, the oligopeptide is deprotected and converted to the appropriate DTPA chelate. However, this methodology has some drawbacks. First, practically only one DTPA molecule can be introduced. This may be problematic in applications were high detection sensitivity is required. Second, since one of the iminoacetic acid groups is used for conjugation, the resulting chelate is less stable than the parent DTPA molecule [Paul-Roth, C. and Raymond, K. N. 1995, Inorg. Chem. 34, 1408, Li, W. P., Ma, D. S., Higginbotham, C., Hoffman, T., Ketring, A. R., Cutler, C. S, and Jurisson, S. S. 2001, Nucl. Med. Biol. 28, 145.]. This may be a serious problem in vivo applications especially in MRI due to the high toxicity of free Gd(III) ion.

A schematic preparation of stable DTPA derivatives applicable to solid phase peptide incorporation have been proposed [U.S. Pat. No. 5,637,759], but the method of their preparation is challenging due to the carboxyl protecting strategy. There, selective deprotection of a single and specific carboxylic acid group out of six of similar reactivities is required. This problem can be avoided by changing the protecting group strategy, but the synthetic route will be considerably longer [WO 03/011115].

SUMMARY OF THE INVENTION

The main object of the present invention is to provide DTPA derivatives which allow solid phase introduction of the chelate to bioactive molecules using a standard oligopeptide synthesizer. The bioconjugates thus obtained are highly suitable for magnetic resonance imaging (MRI), positron emission tomography (PET), single positron emission computed tomography (SPECT) and dissossiation enhanced lanthanide fluorescence immunoassay (DELFIA) as well as target-specific radiopharmaceuticals. The major advantage of the present invention are:

(i) synthesis of the building block is simple and thus these molecules can be synthesized in large scale;

(ii) the blocks can be introduced to the biomolecule structure with standard oligopeptide synthesizer in high efficiency using normal procedures;

(iii) since the metal is introduced after the chain assembly is completed, the molecule synthesized can be used in various applications simply by changing the metal;

(iv) since none of the DTPA carboxylic acid residues are used for conjugation the stability of the chelate does not change;

(v) the chelate formation is considerably faster than in the case of DOTA (the other most commonly used chelator). This is advantageous while working with short-living radioisotopes.

(vi) the labeling reactant can be used in the labeling of a large variety of bioactive molecules such as oligopeptides, steroids and drugs.

In some applications it is advantageous that the chelate is neutral. Then, two of the acetate groups can be substituted with amides. Naturally, the stability of these chelates is lower than that of the corresponding acetates.

Thus, the present invention concerns a labeling reactant of formula (I) or (Ia) suitable for labeling of a biospecific binding reactant

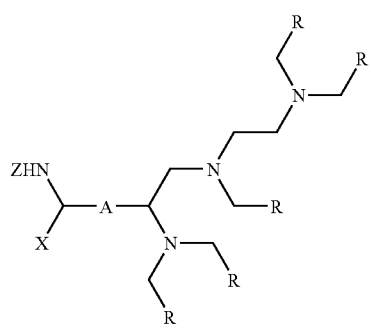

wherein,
—A— is a linker, which is formed from one to ten moieties, each moiety being selected from the group consisting of phenylene, alkyl containing 1-12 carbon atoms, ethynediyl (—C≡C—), ethylenediyl (—C=C—); ether (—O—), thioether (—S—), amide (—CO—NH— and —CO—NR"), carbonyl (—CO—), ester (—COO— and —OOC—), disulfide (—SS—), diaza (—N=N—) or a tertiary amine (—NR"—), where R" represents an alkyl containing less than 5 carbon atoms, each R is independently —COOR' or —CONHR', where R' is an alkyl of 1 to 4 carbon atoms, phenyl or benzyl, which phenyl or benzyl is substituted or unsubstituted;

Z is a transient protecting group;

X is a carboxylic acid, its organic or inorganic salt or active ester or acid halide.

The present invention concerns a method for the preparation of labeling reactants of formula (I) and (Ia) as defined in claim 9.

DETAILED DESCRIPTION OF THE INVENTION

In case R' as defined above is a substituted phenyl or substituted benzyl, the most preferable substituents include chloride.

Where X is an active ester of a carboxylic acid, said ester is preferably an N-hydroxysuccinimido, p-nitrophenol or pentafluorophenol ester.

Where X is an acid halide of a carboxylic acid, said halide is preferably chloride or fluoride.

The transient protecting group Z is preferably fluorenylmethoxycarbonyl (Fmoc); nitrobenzenesulfonyl (Ns); tert-butoxycarbonyl (Boc) or 1,1-dioxobenzo[b]thio-phen-2-yl-methyloxycarbonyl (Bsmoc).

The biospecific binding reactant to be labeled is, for example, an oligopeptide, protein, oligosaccharide, polysaccaride, phospholipid, PNA, LNA, antibody, hapten, drug, receptor binding ligand or lectine. Most preferably, the biospecific binding reactant is an oligopeptide.

The present invention concerns also a method for the preparation of labeling reactants of formula (I) and (Ia)

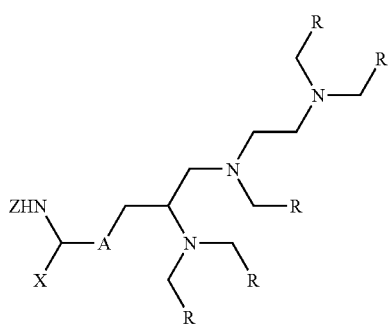

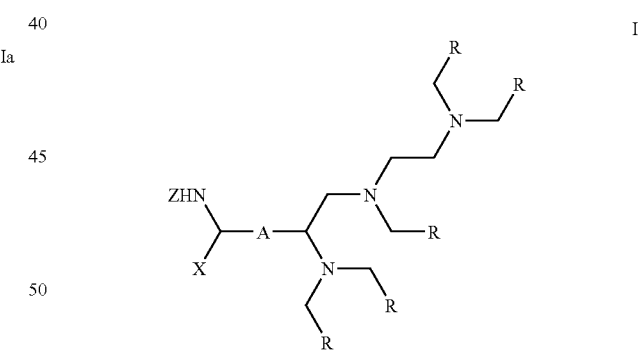

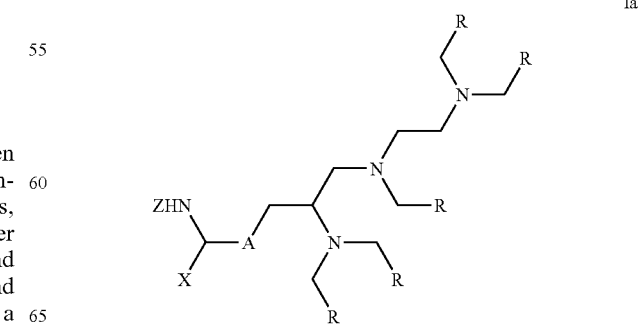

comprising (i) reaction of the molecule of structure formula (II) or (IIa)

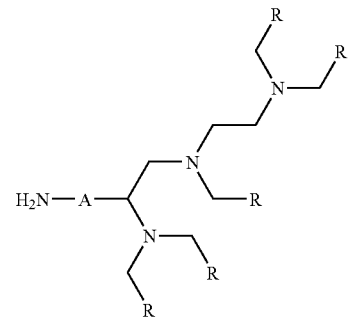

II

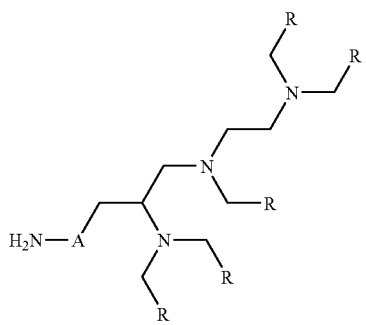

IIa with a compound of the formula (III),

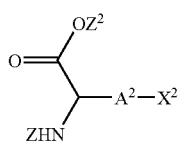

(III)

wherein $Z^2$ is a transient protecting group, most preferably allyl or benzyl, $A^2$ is a linker formed from one to ten moieties, each moiety being selected from the group consisting of phenylene, alkyl containing 1-12 carbon atoms, ethynediyl (—C≡C—), ethylenediyl (—C═C—); ether (—O—), thioether (—S—), amide (—CO—NH— and —NH—CO— and —CO—NR"— and —NR"—CO—), carbonyl (—CO—), ester (—COO— and —OOC—), disulfide (—SS—), diaza (—N═N—) and tertiary amine (—NR"—), where R" represents an alkyl containing less than 5 carbon atoms, $X^2$ carboxylic acid, acid chloride, acid bromide, acid fluoride or an active ester, most preferably pentafluorophenyl or N-hydroxysuccininyl ester, optionally in the presence of an activator to give compound (IV) or (IVa)

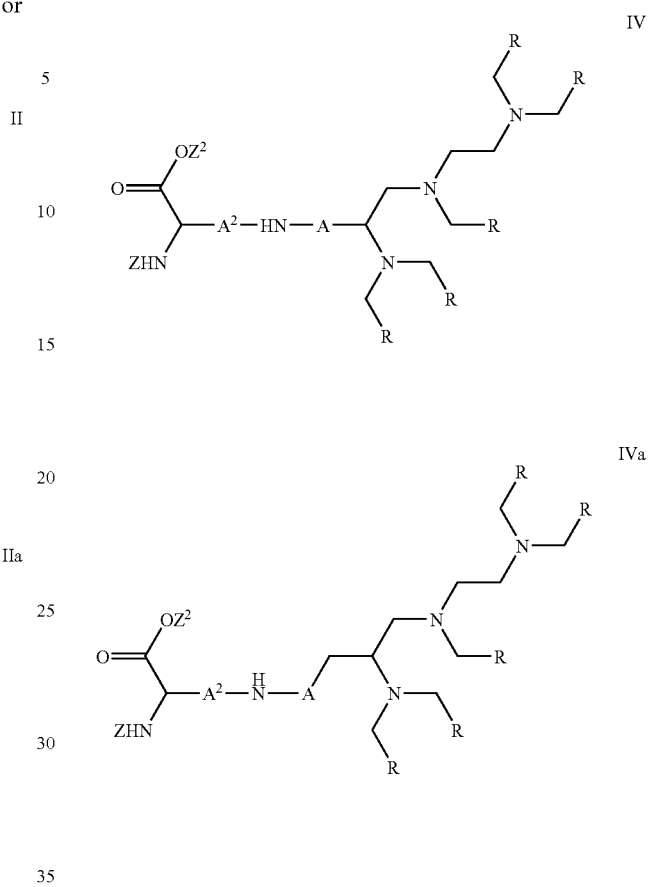

which is deprotected to give compound of formula I or Ia in which X is COOH, after which X optionally is converted to the corresponding organic or inorganic salt or active ester or acid halide.

The invention will be illuminated by the following non-restrictive Experimental Section.

EXPERIMENTAL SECTION

The invention is further elucidated by the following examples. The structures and synthetic routes employed in the experimental part are depicted in Scheme 1. Experimental details are given in examples 1 and 2. Coupling of the oligopeptide building block to oligopeptide structure on solid phase, deprotection and conversion to the corresponding gadolinium(III) chelate is given in Example 3.

Procedures

Adsorption column chromatography was performed on columns packed with silica gel 60 (Merck). Reagents for oligopeptide synthesis were purchased from Nova Biochem. Sodium sulfinate resin (200-400 mesh, 1% DVB, 1.3 mmol $g^{-1}$) was purchased from Tianjin Nankai Hecheng Science & technology Company Limited (China). The oligopeptides were assembled on an Applied Biosystems 433A instrument, using recommended protocols. HPLC purifications were performed using a Shimazu LC 10 AT instrument equipped with a diode array detector, a fraction collector and a reversed phase column (LICHROCART® 125-3 PUROSPHER® RP-18e 5 μm). Mobile phase: (Buffer A): 0.02 M triethylammonium acetate (pH 7.0); (Buffer B): A in 50%

(v/v) acetonitrile. Gradient: from 0 to 1 min 95% A, from 1 to 21 min from 95% A to 100% B. Flow rate was 0.6 mL min$^{-1}$. All dry solvents were from Merck and they were used as received. NMR spectra were recorded on a Bruker 250 spectrometer operating at 250.13 MHz for H. The signal of TMS was used as an internal reference. ESI-TOF mass spectra and IR spectra were recorded on Applied Biosystems MARINER™ and PerkinElmer SPECTRUM™ ONE instruments, respectively.

EXAMPLES

Example 1

The synthesis of penta-tert-butyl 2-{4'-{2-[4-allyloxycarbonyl-4-(fluorenylmethyloxycarbonylamino)]butyrylamido}benzyl}-diethylenetriamine-pentakis(acetate), 2

Fmoc-Glu-OAll (1.31 g, 3.21 mmol), HATU (1.22 g, 1.32 mmol) and DIPEA (0.57 mL, 3.21 mmol) were dissolved in dry DMF (5 mL), and the mixture was stirred for 15 min at RT. Compound 1, disclosed in Corson, D. T., Meares, C. F., 2000, Bioconjugate Chem., 11, 292 (2.50 g, 3.21 mmol; predissolved in 2 mL of dry DMF) was added and the mixture was stirred for an additional 2 h. The mixture was diluted with dichloromethane (50 mL), washed twice with 10% citric acid and dried over Na$_2$SO$_4$. Purification on silica gel (eluent CH$_2$Cl$_2$/MeOH 9:1, v/v) gave 2.84 g (82%) of compound 2. $^1$H NMR (CDCl$_3$): δ 8.31 (2H, br s); 7.75 (2H, d, J 7.3); 7.61 (4H, m); 7.39 (2H, t, J 7.3); 7.30 (2H, m); 7.02 (2H, d, J 8.6); 5.96 (1H, m); 5.89 (1H, m); 5.26 (1H, m); 4.65 (2H, d, J 5.4); 4.41 (2H, m); 4.22 (1H, t, J 6.7); 3.40-2.38 (24H); 1.48 (36H, s); 1.42 (9H, s). ESI-TOF-MS for C$_{64}$H$_{92}$N$_5$O$_{15}$ (M+H)$^+$: calcd, 1170.66; found, 1170.59.

Example 2

The synthesis of penta-tert-butyl 2-{4'-{2-[4-carboxy-4-(fluorenylmethyloxycarbonylamino)]butyrylamido}benzyl}diethylenetriamine-pentakis(acetate), 3

Compound 2 (1.00 g, 0.90 mmol) was dissolved in dry THF (20 mL) and deaerated with argon. Pd(Ph$_3$P)$_4$ (63 mg) and sodium sulfinate resin (1.0 g) were added, and the mixture was stirred for 2 h at RT. The resin was filtered off, washed with THF and the filtrate was concentrated. The residue was dissolved in dichloromethane, washed with 10% citric acid, dried over 4 Å molecular sieves. Concentration in vacuo yielded compound 3. ESI-TOF-MS for C$_{61}$H$_{88}$N$_5$O$_{15}$ (M+H)$^+$: calcd, 1130.63; found, 1130.65.

Example 3

The Synthesis of Oligopeptide Conjugates

A model sequence (RKEMSIKVAVS) was synthesized in 10 μmol scale using Fmoc chemistry and recommended protocols (coupling time 30 min for natural amino acid analogues, and 2 h for 3). One or five blocks 3 was coupled to its carboxy terminus. When the chain assembly was completed, the resin was treated with the mixture of crystalline phenol (75 mg), ethanedithiol (25 μL), thioanisole (50 μL), water (50 μL) and trifluoroacetic acid (1 mL) for 4 h. The resin was removed by filtration, and the solution was concentrated in vacuo. The crude oligopeptide was precipitated with diethyl ether. The precipitate was redissolved in water and treated with gadolinium(III) citrate (5 equiv per ligand). Purification was performed on HPLC.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

Scheme 1

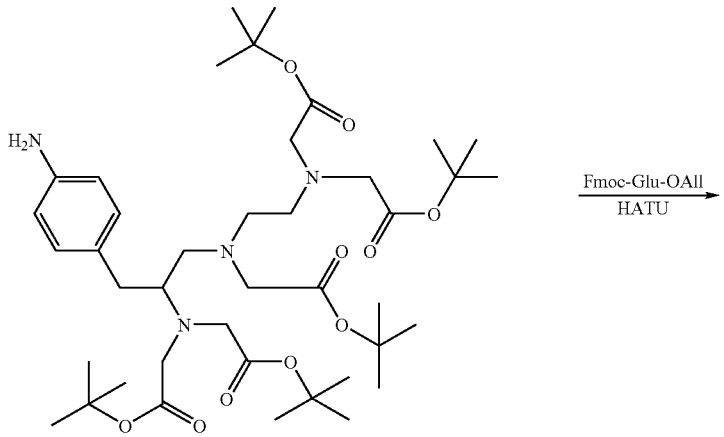

1

-continued
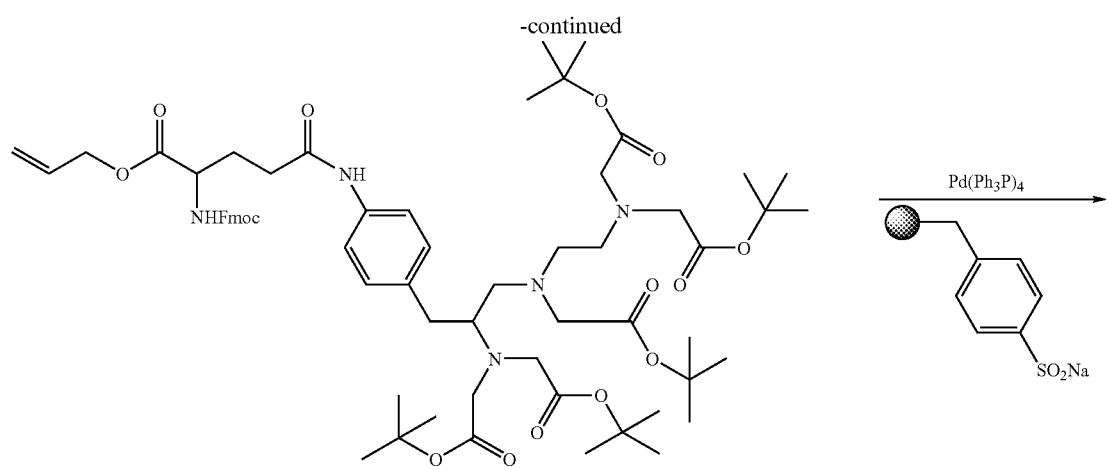
2
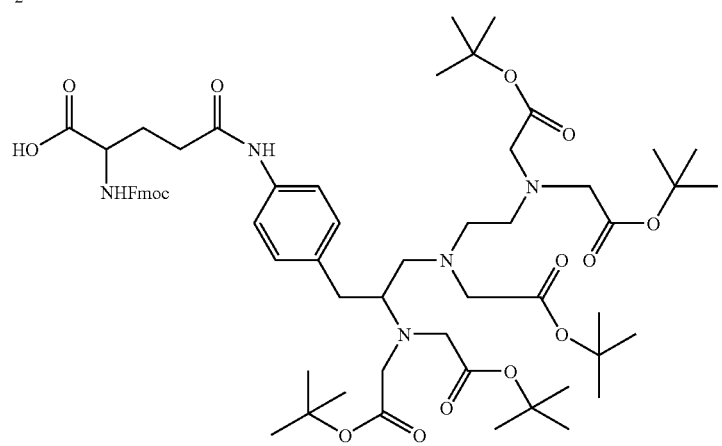
3
What is claimed is:
1. A labeling reactant suitable for labeling of a biospecific binding reactant using solid-phase synthesis, wherein the labeling reactant is penta-tert-butyl 2-{4'-{2-[4-carboxy-4-(fluorenylmethyloxycarbonylamino)]-butyrylamido}benzyl}-diethylenetriamine-pentakis(acetate).
* * * * *